(12) United States Patent
Lindsay

(10) Patent No.: US 10,962,535 B2
(45) Date of Patent: Mar. 30, 2021

(54) POROUS MATERIAL FUNCTIONALIZED NANOPORE FOR MOLECULAR SENSING APPARATUS

(71) Applicant: ARIZONA BOARD OF REGENTS on behalf of ARIZONA STATE UNIVERSITY, Scottsdale, AZ (US)

(72) Inventor: Stuart Lindsay, Phoenix, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 117 days.

(21) Appl. No.: 15/781,948

(22) PCT Filed: Jan. 12, 2017

(86) PCT No.: PCT/US2017/013215
§ 371 (c)(1),
(2) Date: Jun. 6, 2018

(87) PCT Pub. No.: WO2017/123779
PCT Pub. Date: Jul. 20, 2017

(65) Prior Publication Data
US 2018/0356412 A1 Dec. 13, 2018

Related U.S. Application Data

(60) Provisional application No. 62/277,612, filed on Jan. 12, 2016.

(51) Int. Cl.
*C12Q 1/6869* (2018.01)
*G01N 33/543* (2006.01)
(Continued)

(52) U.S. Cl.
CPC ............ *G01N 33/5438* (2013.01); *C12M 1/34* (2013.01); *C12Q 1/001* (2013.01); *C12Q 1/02* (2013.01);
(Continued)

(58) Field of Classification Search
CPC .............. G01N 33/5438; G01N 27/26; G01N 33/48721; C12Q 1/68; C12Q 1/001; C12Q 1/02; C12Q 1/6869; C12M 1/34
See application file for complete search history.

(56) References Cited

U.S. PATENT DOCUMENTS 2,097,634 A   11/1937 Malan et al.
4,868,396 A   9/1989 Lindsay
(Continued)

FOREIGN PATENT DOCUMENTS

EP    0410618 A2   1/1991
EP    1080340 B1   3/2001
(Continued)

OTHER PUBLICATIONS

Z. Tang, et al. ("Gel mesh as "brake" to slow down DNA translocation through solid-state nanopores", Nanoscale, 7(31): p. 13207-13214, (Year: 2015).*
(Continued)

*Primary Examiner* — J. Christopher Ball
(74) *Attorney, Agent, or Firm* — Schwabe, Williamson & Wyatt, P.C.

(57) ABSTRACT

The present disclosure provides systems, devices, and methods that relate to a molecular recognition device configured to at least one of sense, identify and sequence at least one portion of a target molecule, the device comprising (a) a partition having a first side and a second side; (b) at least one constriction having a first end open to the first side and a second end open to the second side; (c) at least one pair of
(Continued)

first and second sensing electrodes arranged within the constriction between the first side and the second side of the partition; and (d) a layer of a porous material at least one of arranged and formed on the first side of the partition.

17 Claims, 4 Drawing Sheets

(51) Int. Cl.

| | | |
|---|---|---|
| C12Q 1/68 | (2018.01) |
| C12M 1/34 | (2006.01) |
| C12Q 1/00 | (2006.01) |
| C12Q 1/02 | (2006.01) |
| G01N 27/26 | (2006.01) |
| G01N 33/487 | (2006.01) |

(52) U.S. Cl.
CPC .............. *C12Q 1/68* (2013.01); *C12Q 1/6869* (2013.01); *G01N 27/26* (2013.01); *G01N 33/48721* (2013.01)

(56) References Cited

U.S. PATENT DOCUMENTS

| | | |
|---|---|---|
| 5,106,729 A | 4/1992 | Lindsay et al. |
| 5,155,361 A | 10/1992 | Lindsay |
| 5,866,805 A | 2/1999 | Han et al. |
| 5,983,712 A | 11/1999 | Lindsay et al. |
| 6,051,825 A | 4/2000 | Lindsay et al. |
| 6,121,611 A | 9/2000 | Lindsay et al. |
| 6,134,955 A | 10/2000 | Han et al. |
| 6,245,204 B1 | 6/2001 | Lindsay et al. |
| 6,673,424 B1 | 1/2004 | Lindsay et al. |
| 6,939,684 B1 | 9/2005 | Beraud et al. |
| 7,687,767 B2 | 3/2010 | Lindsay et al. |
| 7,745,206 B2 | 6/2010 | Wang et al. |
| 8,535,512 B2 | 9/2013 | Walavalkar et al. |
| 8,628,649 B2 | 1/2014 | Lindsay et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyartas et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 9,952,198 B2 | 4/2018 | Lindsay et al. |
| 10,139,417 B2 | 11/2018 | Lindsay et al. |
| 10,145,846 B2 | 12/2018 | Lindsay et al. |
| 10,267,785 B2 | 4/2019 | Lindsay et al. |
| 10,287,257 B2 | 5/2019 | Zhang et al. |
| 10,288,599 B2 | 5/2019 | Gyartas et al. |
| 10,330,632 B2 | 6/2019 | Lindsay et al. |
| 10,336,713 B2 | 7/2019 | Zhang et al. |
| 10,379,102 B2 | 8/2019 | Lindsay et al. |
| 2006/0088470 A1 | 4/2006 | Larsson et al. |
| 2008/0223121 A1 | 9/2008 | Lin et al. |
| 2009/0206025 A1 | 8/2009 | Ichikawa et al. |
| 2010/0084276 A1 | 4/2010 | Lindsay et al. |
| 2012/0276573 A1 | 11/2012 | Vandersarl et al. |
| 2013/0302901 A1 | 11/2013 | Lindsay et al. |
| 2015/0142327 A1 | 5/2015 | Ashcroft et al. |
| 2015/0144506 A1 | 5/2015 | Lindsay et al. |
| 2015/0284791 A1 | 10/2015 | Stolovitzky et al. |
| 2016/0025702 A1 | 1/2016 | Lindsay et al. |
| 2016/0108002 A1 | 4/2016 | Zhang et al. |
| 2016/0177383 A1 | 6/2016 | Ashcroft et al. |
| 2016/0194698 A1 | 7/2016 | Lindsay |
| 2017/0204066 A1 | 7/2017 | Lindsay et al. |
| 2017/0343558 A1 | 11/2017 | Lindsay et al. |
| 2018/0120286 A1 | 5/2018 | Lindsay et al. |
| 2018/0223356 A1 | 8/2018 | Ashcroft et al. |
| 2018/0224422 A1 | 8/2018 | Lindsay et al. |
| 2018/0299424 A1 | 10/2018 | Takulapalli et al. |
| 2019/0195856 A1 | 6/2019 | Zhang et al. |
| 2019/0195884 A1 | 6/2019 | Lindsay et al. |
| 2019/0242885 A1 | 8/2019 | Lindsay et al. |
| 2019/0250127 A1 | 8/2019 | Zhang et al. |
| 2019/0256616 A1 | 8/2019 | Zhang et al. |
| 2019/0317040 A1 | 10/2019 | Lindsay et al. |
| 2019/0317072 A1 | 10/2019 | Gyarfas et al. |

FOREIGN PATENT DOCUMENTS

| | | |
|---|---|---|
| JP | 2002515592 A | 5/2002 |
| WO | 1999006793 A1 | 2/1999 |
| WO | 1999060330 A1 | 11/1999 |
| WO | 2004059243 A1 | 7/2004 |
| WO | 2008124706 A9 | 5/2009 |
| WO | 2009117517 A2 | 9/2009 |
| WO | 2009117522 A2 | 9/2009 |
| WO | 2010042514 A1 | 4/2010 |
| WO | 2011097171 A1 | 8/2011 |
| WO | 2013116509 A1 | 8/2013 |
| WO | 2013148344 A1 | 10/2013 |
| WO | 2013151756 A1 | 10/2013 |
| WO | 2013180819 A1 | 12/2013 |
| WO | 2014059144 A1 | 4/2014 |
| WO | WO 2014/059046 A1 | 4/2014 |
| WO | 2014138253 A1 | 9/2014 |
| WO | 2014165168 A1 | 10/2014 |
| WO | 2014190299 A2 | 11/2014 |
| WO | 2014194246 A1 | 12/2014 |
| WO | 2015010904 A1 | 1/2015 |
| WO | 2015081294 A2 | 6/2015 |
| WO | 2015131073 A1 | 9/2015 |
| WO | 2015161119 A1 | 10/2015 |
| WO | 2015171930 A1 | 11/2015 |
| WO | 2016077263 A1 | 5/2016 |
| WO | 2018039129 A1 | 3/2018 |
| WO | 2018064078 A1 | 4/2018 |

OTHER PUBLICATIONS

Z. Chen, et al. "DNA translocation through an array of kinked nanopores", Nature Materials, 9(8): p. 667-675, Aug. (Year: 2010).*
N. Liu, et al."Synthesis and characterization of highly ordered mesoporous thin films with—COOH terminated porous surfaces", Chemical Communications, (3): p. 370-371, Jan. 2003.*
N. Malmstadt, et al. ("Long-Lived Planar Lipid Bilayer Membranes Anchored to an In Situ Polymerized Hydrogel", Advanced Materials, 20(1): p. 84-89, Jan. 2008.*
Bai, J. et al., "Fabrication of sub-20 nm nanopore arrays in membranes with embedded metal electrodes at wafer scales", Nanoscale, May 2014, vol. 6, No. 15, pp. 8900-8906 <DOI:10.1039/C3NR06723H>.
Bhatia, R. et al., "Aqueous Sol-Gel Process for Protein Encapsulation", Chemical Materials, Jul. 2000, vol. 12, No. 8, pp. 2434-2441 <DOI:10.1021/cm000260f>.
Briggs, K. et al., "Kinetics of nanopore fabrication during controlled breakdown of dielectric membranes in solution", Nanotechnology, Feb. 2015, vol. 26, No. 8, article 084004, 10 pages <DOI:10.1088/0957-4484/26/8/084004>.
Cherf, G. et al., "Automated forward and reverse ratcheting of DNA in nanopore at 5-Å precision", Nature Biotechnology, Apr. 2012, vol. 30, No. 4, pp. 344-348 <DOI:10.1038/nbt.2147>.
Ellerby, L. et al., "Encapsulation of proteins in transparent porous silicate glasses prepared by the sol-gel method", Science, Feb. 1992, vol. 255, No. 5048, pp. 1113-1115 <DOI:10.1126/science.1312257>.
Fologea, D. et al., "Detecting single stranded DNA with a solid state nanopore", Nanoletters, Aug. 2005, vol. 5, No. 10, pp. 1905-1909 <DOI:10.1021/nl051199m>.
Nisticò, R. et al., "Selective porous gates made from colloidal silica nanoparticles", Beilstein Journal of Nanotechnology, Nov. 2015, vol. 6, pp. 2105-2112 <DOI:10.3762/bjnano.6.215>.
Nivala, J. et al., "Unfoldase-mediated protein translocation though an alpha-hemolysin pore", Nature Biotechnology, Mar. 2013, vol. 31, No. 3, pp. 247-250 <DOI:10.1038/nbt.2503>.

(56) References Cited

OTHER PUBLICATIONS

Tang, Z. et al., "Gel mesh as "brake" to slow down DNA translocation through solid-state nanopores", Nanoscale, Jul. 2015, vol. 7, No. 31, pp. 13207-13214 <DOI:10.1039/C5NR03084F>.
Wanunu, M. et al., "Electrostatic focusing of unlabelled DNA into nanoscale pores using a salt gradient", Nature Nanotechnology, Feb. 2010, vol. 5, pp. 160-165 <DOI:10.1038/NNAN0.2009.379>.
Yang, J. et al., "Rapid and precise scanning helium ion microscope milling of solid-state nanopores for biomolecule detection", Nanotechnology, Jun. 2011, vol. 22, No. 28, pp. 285310-285320 <DOI:10.1088/0957-4484/22/28/285310>.
European Patent Office, Supplementary European Search Report and Opinion for 17738949.1, 6 pages, dated May 24, 2019.
Patent Cooperation Treaty, International Searching Authority, International Preliminary Report on Patentability for PCT/US2017/013215, 10 pages, report dated Jul. 17, 2018, opinion dated Mar. 31, 2017.
Patent Cooperation Treaty, International Searching Authority, International Search Report for PCT/US2017/013215, 3 pages, dated Mar. 31, 2017.
U.S. Application No. 16/293,546.
Wang, Y et al., "The evolution of nanopore sequencing", Fronteirs in Genetics, vol. 5, No. 449, Jan. 2015, pp. 1-20.

\* cited by examiner

US 10,962,535 B2

POROUS MATERIAL FUNCTIONALIZED NANOPORE FOR MOLECULAR SENSING APPARATUS

CROSS REFERENCE TO RELATED APPLICATIONS

This application is a national phase filing under 35 USC §371 of International PCT Application for PCT/US2017/013215, filed on Jan. 12, 2017, which claims the priority to and the benefit of U.S. Provisional Application No. 62/277,612, filed on Jan. 12, 2016, the disclosure of each of which is hereby incorporated by reference in its entirety.

GOVERNMENT RIGHTS

This invention was made with government support under R01 HG006323 awarded by The National Institutes of Health. The government has certain rights in the invention.

BACKGROUND

At the present time, there is no scalable method for making nanopores (which is also be referred to as constrictions) in solid membranes for single molecule analysis. Nanopores can be drilled one at a time using electron beams or with an ion-beam that can be focused to a fine point. Electrochemical breakdown of dielectric films can produce very small pores without the need of energetic beams, but each site at which a pore is made must be addressed individually. Reactive ion etching (RIE) is a fast, parallel process in which many pores can be cut in one step after a protective layer is opened using lithography techniques. However, current limitations of lithography make it very difficult to drill pores by ME that are smaller than about 20 nm in diameter—such a diameter being too large to prevent folded DNA from entering pore, for example, or too large to trap a protein against the pore for controlling the passage of a polymer.

SUMMARY

Some embodiments of the disclosure herein provide a method of circumventing above-noted problem(s) by, for example, placing a layer of a porous material such as a gel and/or aggregate of fine particles on a side of a nanopore which, in some instances, can act as a trap for small proteins.

In one aspect, a molecular device is configured to at least one of sense, identify and sequence at least one portion of a target molecule is provided, where the device includes a partition having a first side and a second side, the partition characterized by a thickness associated therewith, and at least one constriction having a first end open to the first side and a second end open to the second side. The at least one constriction includes an interior wall, the at least one constriction characterized by a diameter, a perimeter, and a length corresponding to at least the thickness. The diameter is selected to pass therethrough target molecules from the first side to the second side, a single target molecule at a time. The device can also include at least one pair of first and second sensing electrodes arranged within the constriction between the first side and the second side of the partition. The first electrode is arranged along at least a portion of the perimeter of the interior wall at a first position along the length of the constriction, and the second electrode is arranged along at least a portion of the perimeter of the interior wall at a second position along the length of the constriction spaced away from the first position establishing a gap therebetween. In addition, the partition material in the gap can include an insulating material. The device can further include a layer of a porous material (e.g., a gel, an aggregate of nanoparticles, or a combination thereof), where the layer of the porous material is at least one of arranged and formed on the first side of the partition. The porous material includes a plurality of pores, and is configured such that a target molecule passes through at least a portion of the porous material to reach the nanopore (i.e., constriction). In some embodiments, the average diameter of pores of the porous material is less than the diameter of the constriction.

In another aspect, a molecular arranging or filtering device is provided, which is configured for directing a molecule into a constriction. The device includes a partition having a first side and a second side, the partition characterized by a thickness associated therewith. At least one constriction has a first end open to the first side and a second end open to the second side, and a layer of a porous material (e.g., a gel, an aggregate of nanoparticles, or a combination thereof) at least one of arranged and formed on the first side of the partition. In some aspects of the device, the porous material includes a porosity including a plurality of pores, and the porous material is configured such that a target molecule passes through at least a portion of the porous material to reach the constriction. In some embodiments, the average diameter of pores of the porous material is less than the diameter of the constriction.

In some embodiments of any one of the above aspects, the amount of the porous material is such that a height of the layer of the porous material above the first side of the partition is less than about 5 microns.

In some embodiments of any one of the above aspects, the amount of the porous material is such that the height of layer of the porous material above the first side of the partition is between about 10 nm to about 5 microns.

In some embodiments of any one of the above aspects, the porous material includes a gel, an aggregate of nanoparticles, or a combination thereof.

In some embodiments of any one of the above aspects, the porous material includes a hydrogel.

In some embodiments of any one of the above aspects, the porous material includes a silicate gel.

In some embodiments of any one of the above aspects, the layer of the porous material is formed on the first side of the partition by hydrolysis or spin-coating.

In some embodiments of any one of the above aspects, the average diameter of the pores of the porous material is about 10 nm or less.

In some embodiments of any one of the above aspects, the average diameter of the pores in the porous material is smaller than the diameter of a motor protein used to control the motion of a polymer.

In some embodiments of any one of the above aspects, the first or second electrode comprises a metal or doped semiconductor.

In some embodiments of any one of the above aspects, the device includes a plurality of constrictions. The plurality of constrictions can be arranged in an array or a random manner.

In some embodiments of any one of the above aspects, the partition includes a membrane.

The present disclosure also provides a method of making the devices described herein, including: (i) providing a partition having a first side and a second side; (ii) forming at least one constriction through the partition; and (iii) forming a layer of a porous material on the first side of the partition. In some embodiments, the method further includes forming spaced apart first and second sensing electrodes on the first side of the partition. In some embodiments, forming first and second sensing electrodes comprises performing photolithography or electron-beam lithography and depositing a metal. In some embodiments, forming the at least one constriction comprises milling a hole in the partition. Milling the hole can be performed via reactive ion etching, laser drilling, or focused ion beam drilling.

In some embodiments, the method of making the device can further include positioning the partition such that a salt solution is on the first side of the partition and a metal plating solution is on the second side of the partition; and applying a current such that the metal plating solution passes through the constriction and plates onto the first and second sensing electrodes, thereby reducing at least one of: (a) a dimension of the constriction, and (b) a gap between the first and second sensing electrodes. In some embodiments, the method includes plating the metal onto the first and second sensing electrodes until a predetermined amount of current is obtained between the two sensing electrodes. In some embodiments, the method includes stripping the plated metal to thereby enlarge a gap between the first and second sensing electrodes, after said predetermined amount of current has been obtained. In some embodiments, forming the layer of the porous material comprises spin-coating a precursor of the porous material on the first side of the partition. In some embodiments, forming the layer of the porous material includes hydrolyzing tetramethylorthosilicate or tetraethylorthosilicate.

The present disclosure also provides a method for at least one of sensing, identifying, and sequencing at least a portion of a target molecule as the target molecule translocates through a constriction. The target molecule can be a DNA or RNA molecule, or a portion thereof. In one aspect, a method includes (i) providing an apparatus including a molecular recognition device described herein, the device being located in the apparatus such that a first chamber is located on the first side of the device and a second chamber is located on the second side of the device; (ii) introducing the target molecule into the second chamber; (iii) electrophoresing the target molecule so that it translocates through the constriction; and (iv) detecting an electrical signal when at least a portion of the target molecule is passing through the constriction.

In some embodiments, the method can further include threading a leading end of the target molecule through the constriction and into the first chamber, detecting said electrical signal. The electrical signal can be an electrical current or voltage.

In some embodiments, the method can further include: recording the electrical current as a function of time; and obtaining at least one parameter reflective of an identification of a particular portion of the target molecule from the recorded electrical current. The at least one parameter is selected from the group consisting of charge, duration of current signal, shape of current signal, and decay of current. In some embodiments, the method can further include comparing the at least one parameter with a predetermined threshold to determine whether the particular portion has been recognized. In some embodiments, the method can further include detecting electrical current from a same portion of a predetermined number of copies of the target molecule to thereby improve recognition accuracy of the portion.

The method can be configured for high-throughput sensing, identifying, or sequencing the target molecule.

These and other embodiments, advantages and objects of the disclosure will become even more clear with reference to the below information and attached drawings, a brief description of which is provided below.

DETAILS OF SOME OF THE EMBODIMENTS

Figure 1A:
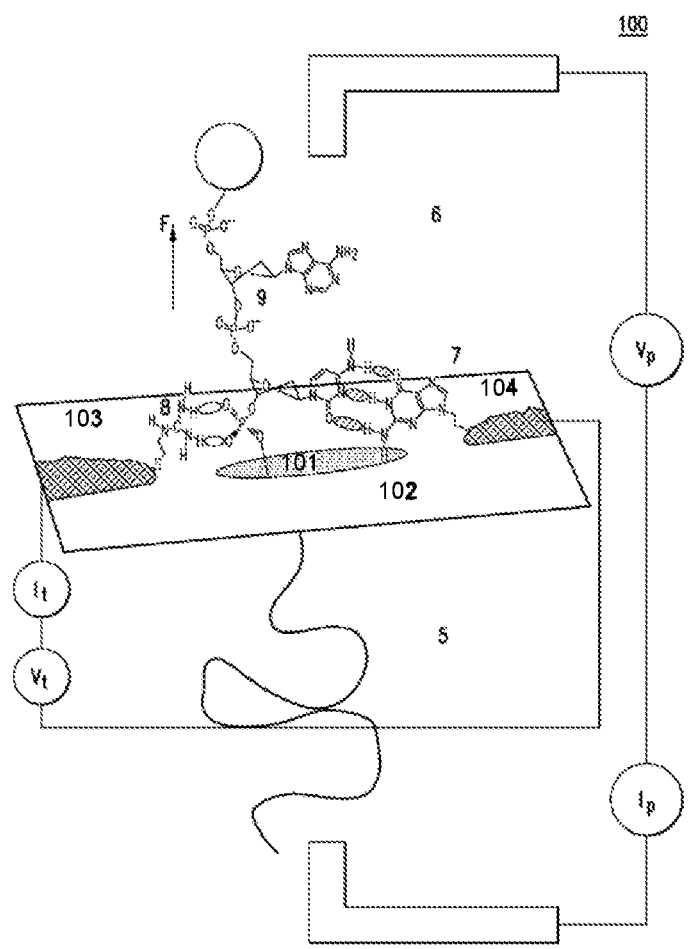
FIG. 1A illustrates a system for at least one of sensing, identifying and sequencing a target molecule.
Figure 1B:
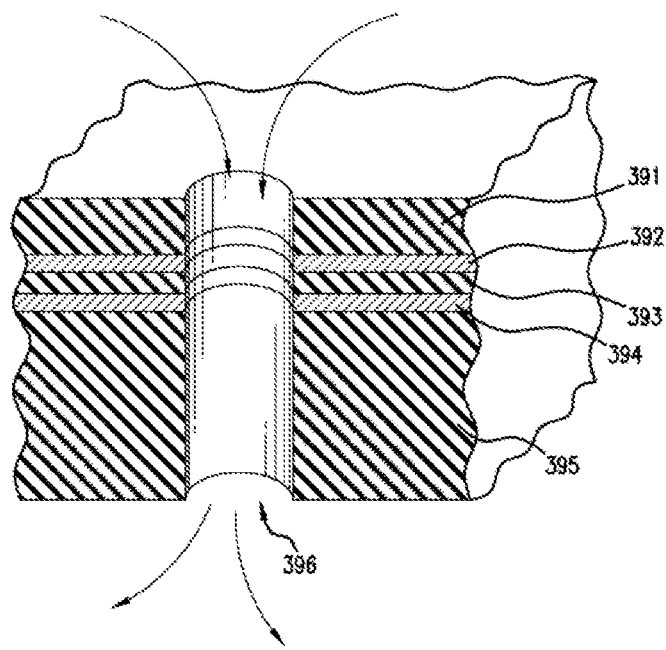
FIG. 1B illustrates a partition/nanopore structure according to some embodiments, for aiding in at least one of sensing, identifying and sequencing a target molecule.

US patent publication no. 2010/0084276 entitled, "DEVICES AND METHODS FOR TARGET MOLECULE CHARACTERIZATION" ("the '276 publication"), hereby incorporated by reference in its entirety, discloses embodiments directed to systems, methods and devices for sequencing molecules (e.g., polymers such as DNA). Such embodiments include a nanopore into which a pair of electrodes is incorporated, as set out in FIGS. 1A and 1B. FIG. 1A is an apparatus 100 configured to read molecules (e.g. DNA bases), by measuring tunneling current. A constriction in the form of a nanopore 101, is formed in the device. In some embodiments, the device includes a chip 102. The top of the chip 102 includes a first side while the bottom of the chip 102, which is hidden from view in FIG. 1A, includes a second side. Thus, the device can be considered to include a partition having a first side and a second side, and the molecule translocates from one side of the partition to the other side of the partition, via the constriction/nanopore 101. First and second electrically conductive sensing electrodes, 103, 4104 which are spaced apart from one another by a gap, are provided adjacent the nanopore 101 on the first side of the chip 102 (or within the pore as shown in FIG. 1B). The gap between the first and second electrodes can be between 1.0-5.0 nm. though larger gaps can he possible. The first and second sensing electrodes are preferably formed of gold, though they can instead be formed of other suitable electrically conductive materials such as (but not limited to) metals, alloys, doped semiconductors, and conductive polymers.

The chip 102 is mounted in the device 100 such that the chip's first side (also sometimes referred to as a "top" side) is exposed to a first fluid chamber 6 ((also sometimes referred to as an "upper chamber") and the chips second side (also sometimes referred to as a "bottom" side) is exposed to a second fluid chamber ((also sometimes referred to as a "lower chamber"). As seen in FIG. 1A, the second fluid chamber 6 contains the molecule 9 to be read, while the first fluid chamber receives the molecule 9 translocating through the nanopore 101 which forms a passage between the two fluid chambers 5, 6.

On the first side of the nanopore 101, a first affinity element 8 is tethered to the first sensing electrode 103 via a first flexible linker. The term "linker" as used herein can refer to a chemical designed so as to permit adequate motion of the affinity element to self-assemble on the target while remaining in electrical communication with an electrode. The first flexible linker itself can be bonded to the first electrode via an electrode attachment molecule, such as a thiol. For example, in the first affinity element 8 can include guanidinium or a guanidinium derivative such as guanidinoethyldisulfide. Guanidinium performs the function of grabbing the phosphate backbone of the DNA 9 and thus serves as "phosphate grabber."

On the second side of the nanopore, a second affinity element 7 is tethered to the second sensing electrode 4104 via a second flexible linker. The second flexible linker itself can he bonded to the second electrode via an electrode attachment molecule, as described above. The second affinity element 7 can include a base reader which is configured to recognize one of the four bases on the DNA 9. In general, both the phosphate grabber and the base reader form chemical bonds that are readily broken at room temperature. Thus, the bonds formed during translocation are made and broken on a timescale that permits rapid binding and release of the target while still allowing for detection and measurement of a tunneling current.

FIG. 1B illustrates a cross-section of a nanopore structure where electrodes 392 and 394 are placed along the inside wall of the nanopore 396. As shown, the device includes top layer of insulation 391, a first metal or doped semiconductor layer 392, a second layer of insulation 393, a second metal or doped semiconductor layer 394, and an insulating substrate 395 on which the structure is formed. The size of the gap between the electrodes 392 and 394 is determined by the thickness of the second layer of insulation 393. The structure is assembled by planar deposition of alternating conducting and insulating layers on the substrate, followed by formation of a channel/nanopore 396 through the entire structure.

Figure 1C:
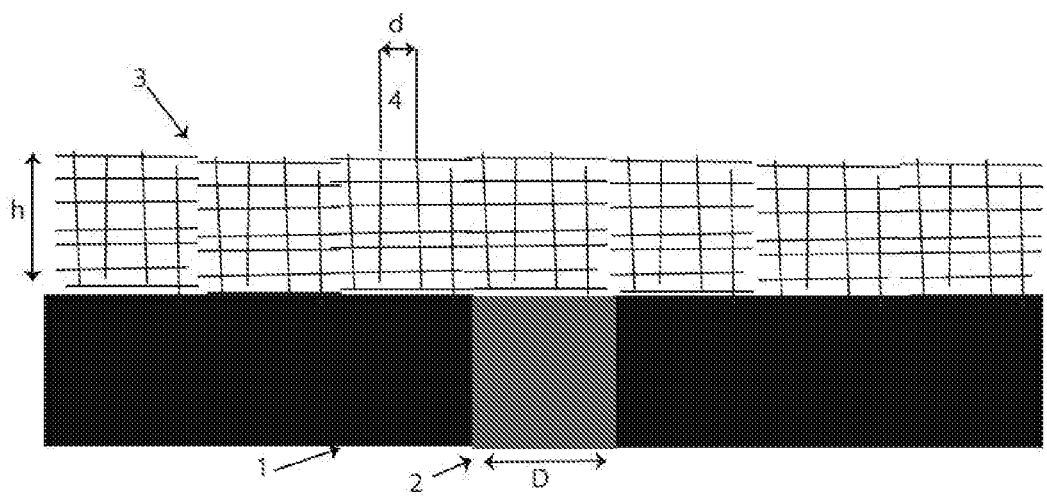
FIG. 1C illustrates a gel and/or aggregate with a pore size d, less than the diameter, D, of a nanopore formed in a solid membrane and located on one side of the membrane, according to some embodiments of the present disclosure.

Some embodiments of the present disclosure are directed to systems like those shown and described in FIGS. 1A-B, but with a modified nanopore/partition/functionality as set out in FIG. 1C. As shown, in FIG. 1C, a solid membrane 1 (i.e., partition) through which is drilled a nanopore 2 of diameter D. The solid membrane/partition can be any material readily processed by semiconductor manufacturing methods including, but not limited to, silicon nitride, silicon dioxide, silicon, hafnium oxide, or other semiconductors, oxides or chalcogenides, including the arrangements shown in FIGS. 1A-B.

In such embodiments as those set out in FIG. 1C, a layer of a porous material 3 is included and arranged or otherwise formed on a first side of the support/partition. In some embodiments, the thickness of the layer of the porous material, h, can be between about 10 nm and about 5000 nm. In some embodiments, the average pore diameter in the porous material, d 4, be less than the diameter of the nanopore 2, D.

Accordingly, one aspect of the disclosure relates to a molecular recognition device configured to at least one of sense, identify and sequence at least one portion of a target molecule. The molecular recognition device includes: (a) a partition having a first side and a second side, the partition characterized by a thickness associated therewith; (b) at least one constriction having a first end open to the first side and a second end open to the second side; (c) at least one pair of first and second sensing electrodes arranged within the constriction between the first side and the second side of the partition; and (d) a layer of a porous material at least one of arranged and formed on the first side of the partition. In some embodiments, the at least one constriction includes an interior wall, the at least one constriction characterized by a diameter, a perimeter, and a length corresponding to the thickness, and the diameter is selected to pass therethrough target molecules from the first side to the second side, a single target molecule at a time. In some embodiments, the first electrode is arranged along at least a portion of the perimeter of the interior wall at a first position along the length of the constriction, the second electrode is arranged along at least a portion of the perimeter of the interior wall at a second position along the length of the constriction spaced away from the first position establishing a gap therebetween, and a partition material in the gap includes an insulating material. In some embodiments, the porous material includes a porosity including a plurality of pores. In some embodiments, the porous material is configured such that a target molecule passes through at least a portion of the porous material to reach the at least one constriction. In some embodiments, the average diameter of the pores of the porous material is less than the diameter of the at least one constriction. In some embodiments, the average diameter of the pores of the porous material is smaller than the diameter of a motor protein used to control the motion of a polymer. In some embodiments, the partition can include a membrane.

Another aspect of the disclosure relates to a molecular arranging or filtering device configured for directing a molecule into a constriction. The molecular arranging or filtering device includes: (a) a partition having a first side and a second side, the partition characterized by a thickness associated therewith; (b) at least one constriction having a first end open to the first side and a second end open to the second side; and (c) a layer of a porous material at least one of arranged and formed on the first side of the partition. In some embodiments, the porous material includes a porosity including a plurality of pores. In some embodiments, the porous material is configured such that a target molecule passes through at least a portion of the porous material to reach the at least one constriction. In some embodiments, the average diameter of the pores of the porous material is less than the diameter of the at least one constriction. In some embodiments, the average diameter of the pores of the porous material is smaller than the diameter of a motor protein used to control the motion of a polymer. In some embodiments, the partition can include a membrane.

The porous material can include a gel, an aggregate of nanoparticles, or a combination thereof. The gel can include a polymer, e.g., a hydrophilic polymer such as (but not limited to) polyacrylamide, polyacrylic acid, polyoxazylene. In some embodiments, the gel can include a hydrogel. A hydrogel can include polyvinyl alcohol, sodium polyacrylate, acrylate polymers, or copolymers with an abundance of hydrophilic groups. In some embodiments, the gel can include a silicate gel. As an alternative, or as an addition, a sieving action can be achieved using an aggregate of nanoparticles. The nanoparticles can be between about 1 nm and about 100 nm in diameter, forming channels between the nanoparticles of diameters from less than a nanometer to over ten nanometers. The nanoparticles can have a diameter in the range of about 10 nm to about 500 nm, e.g., about 10 nm to about 400 nm, about 10 nm to about 300 nm, about 10 nm to about 200 nm, about 10 nm to about 100 nm, about 50 nm to about 200 nm. The nanoparticles can include a polymer (e.g., poly(methyl methacrylate)), metal oxide (e.g., $TiO_2$), semiconductor oxide (e.g., GeO), glass (e.g., $SiO_2$), or a combination thereof.

A first affinity element can be tethered to the first sensing electrodes. Similarly, a second affinity element can be tethered to the second sensing electrodes. Each affinity element may be connected to its corresponding electrode via one or more intermediary compounds, such as a linker molecule, which itself typically is connected to the electrode via an electrode attachment molecule, such as a thiol. The first and second affinity elements are configured to temporarily form hydrogen bonds with first and second portions of the molecule as the latter passes through the constriction. During translocation, the electrodes, affinity elements and first and second portions of the target molecule complete an electrical circuit and allow a measurable electrical current to pass between the first and second electrodes. The time-varying nature of this electrical current, and the specific affinity elements employed, allow one to characterize the first and second portions of the target molecule.

The device can include at least one constriction, at least 10 constrictions, or at least 100 constrictions. For example, the device can include 10 to 1000 constrictions, 10 to 500 constrictions, or 100 to 500 constrictions, thereby permitting high-throughput detection of the target molecules. In some embodiments, the plurality of constrictions can be arranged in an array or a random manner.

Methods for forming a gel and/or aggregate with very small pores include aqueous phase sol-gel chemistry in which tetramethylorthosilicate (TMSO) or tetraethylorthosilicate (TEOS) are hydrolyzed in the presence of a catalyst such as HCl to form a silicate network, hydrolysis of sodium silicate or formation of a nanoparticle aggregate by spinning on a solution of colloidal nanoparticles. In this way, gels and/or aggregates are readily formed with mean pore diameters of about 10 nm, with many openings in the network being less than this mean value. Spin coating of material readily forms films as thin as about 50 nm or as thick as about 5000 nm through application of successive layers.

The sensing electrodes can be formed by methods known in the art, such as those performed in a cleanroom environment. For example, the sensing electrodes can be formed by photolithography and/or electron-beam lithography followed by metal or doped semiconductor deposition. Metal or doped semiconductor can be deposited by processes known in the art including, but not limited to, thermal evaporation, electron-beam evaporation, or sputtering.

The constrictions can be formed by methods known in the art including, but not limited to, reactive ion etching, laser drilling, or focused ion-beam milling.

Figure 2:
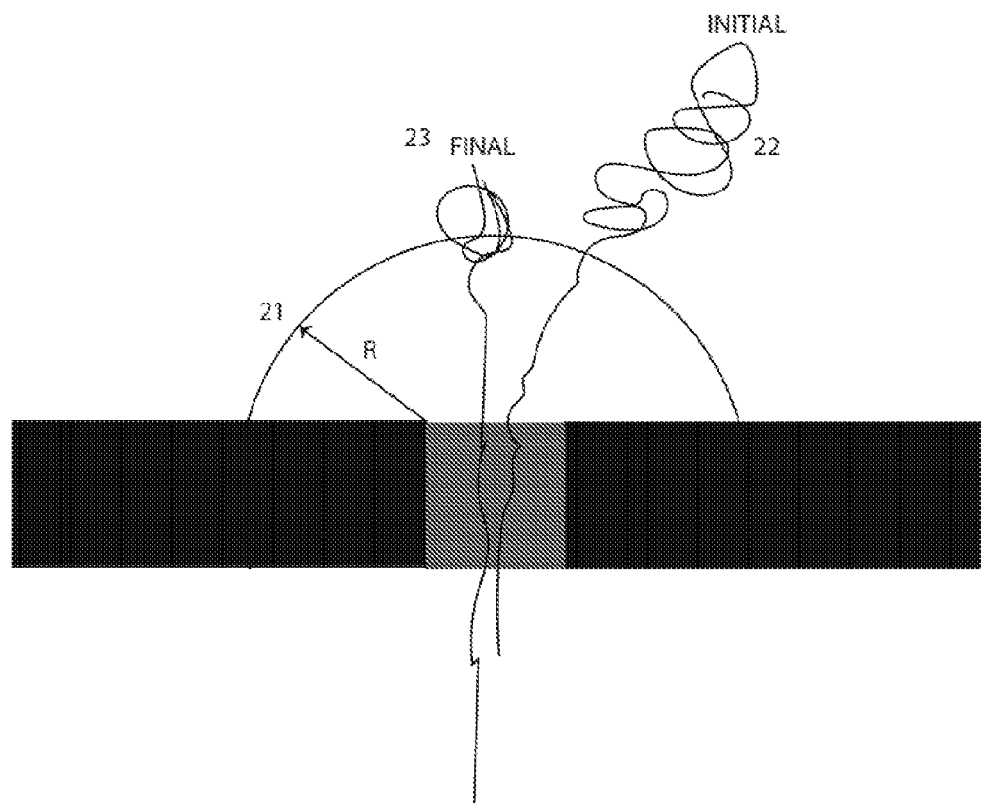
FIG. 2 illustrates a polymer is pulled in towards the center of a nanopore as the charged polymer is captured by the high field region that extends a distance R from the center of the pore, according to some embodiments of the present disclosure.
Figure 5:
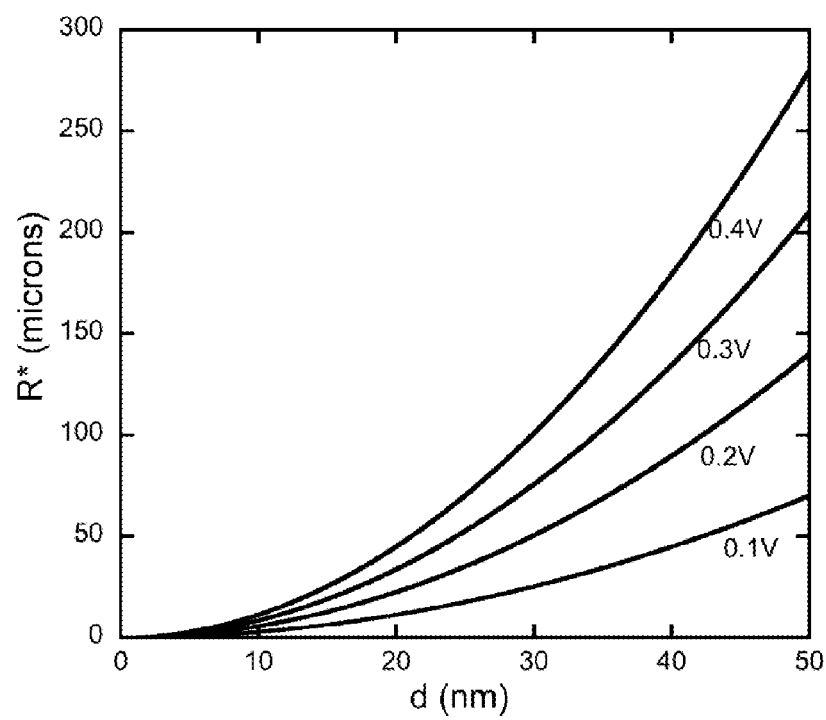
FIG. 5 illustrates the relationship of R to d, according to some embodiments, where R varies with d for a pore thickness of 30 nm and voltages between 0.1 and 0.4V, according to some embodiments of the present disclosure.

In some embodiments, advantages arise when the gel or aggregate pore size is reduced to 10 nm or less. The electric field that captures charged molecules in solution extends a distance R 21 from the center of the nanopore where $$R = \frac{D^2 \mu}{8 l D_{dif}} \Delta V$$

where D is the pore diameter, l the pore length, µ the electrophoretic mobility of the target molecule (e.g., a polymer), $D_{dif}$ the diffusion constant of the target molecule and ΔV the voltage applied across the nanopore. For a long DNA molecule (e.g., lambda DNA), a pore of 12 nm diameter in a membrane of 50 nm thickness with 0.1V applied, R is about 1.6 µm (see also FIG. 5). Thus the capture zone for charged molecules is a hemisphere centered on the pore with a radius of one or up to a few microns. Once a polymer enters this hemisphere, the electric field gradient perpendicular to the pore axis tends to pull the target molecule to the middle of the pore as shown by the polymer positions labeled "INITIAL" 22 and "FINAL" 23 in FIG. 2.

Figure 3:
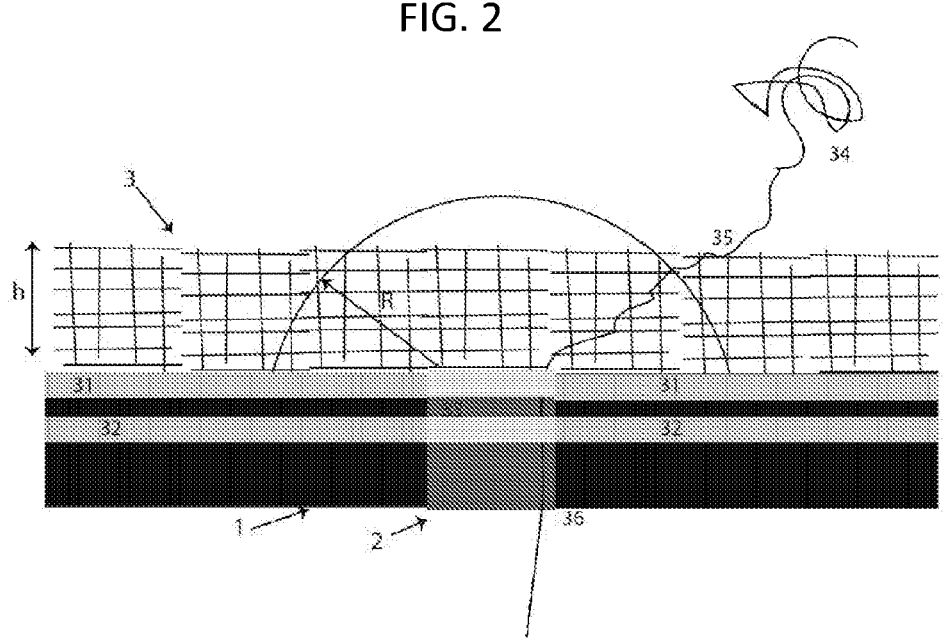
FIG. 3 illustrates the use of a gel and/or aggregate on one side of the pore, according to some embodiments, which is configured to retain the polymer trapped most probably to one side of the pore, thus forcing it to interact with electrodes incorporated in the pore, according to some embodiments of the present disclosure.

If, the target molecule 34 enters into the pores of a gel (FIG. 3) at the edge of the capture region 35 then it is constrained to approach the pore from one edge since it can no longer be moved over the middle of the pore. Since most of the area of capture is exposed away from the middle of the pore (for h<R) the most frequent events will be those in which the target molecule approaches the pore from one side. Reference numerals 31 and 32 are metal layers separated by a thin layer of dielectric 33 to form an exposed tunnel gap in the nanopore. With the target molecule 34 pulled in from the side of the nanopore, it is more likely to be pulled through the pore along one side 36 and thus contact the electrodes 31 and 32. In some embodiments, h<R, so that the capture rate won't be diminished, as diffusion of target molecules into the porous material will be slow. Accordingly, in some embodiments, h is less than a few microns, and in some embodiments, less than 5 microns.

Figure 4:
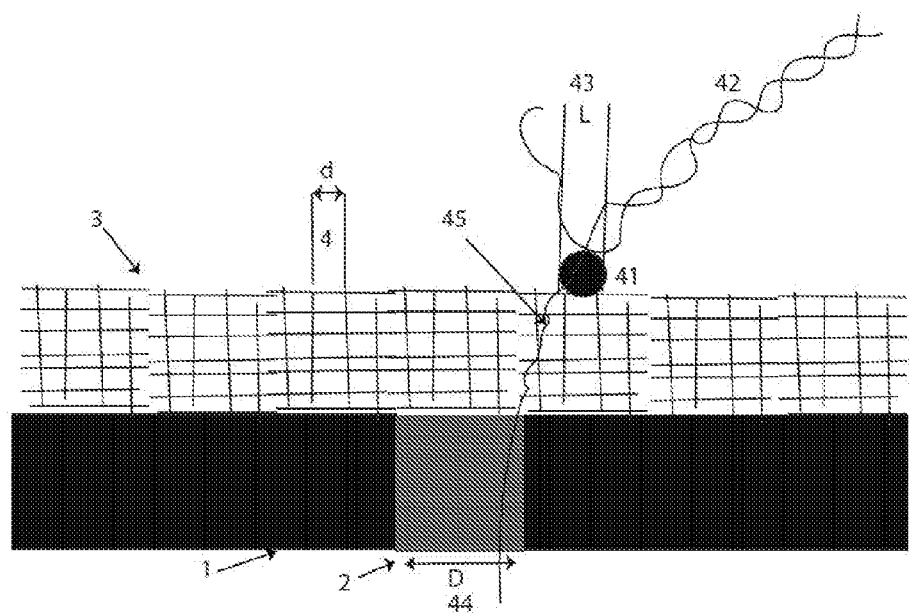
FIG. 4 illustrates the trapping of a protein of diameter L on one side of the pore by the fine mesh of the gel and/or aggregate (d<L) in apparatuses according to some embodiments. Normally, the protein would pass through the pore (L<D), according to some embodiments of the present disclosure.

Another advantage according to some embodiments, compared to using small nanopores without a layer of a porous material formed thereon, corresponds to being able to trap proteins against thin gel layers like those described here. The small-pore silicate aggregates described here are capable of trapping small proteins. For example, a polymerase complexed with DNA has been used to regulate the motion of DNA through a nanopore for sequencing. An unfoldase has been used for pulling proteins through a nanopore. For such techniques, the nanopore diameter can be smaller than the diameter of the protein, so that the protein remains jammed up against one side of the pore. Since typical motor proteins have a diameter of between 5 and 10 nm, pores as large as 20 nm in diameter produced by RIE will not suffice to capture the proteins. Referring to FIG. 4, if the mesh size d (4) in the gel or aggregate layer is smaller than the diameter L 43 of the protein 41, then the protein will be trapped even if the nanopore diameter D 44 is much bigger than L. Illustrating this for the case of DNA sequencing, the protein 41 could be a helicase, and it would be complexed with a double stranded DNA 42 with the singe stranded end 45 passing through the helicase pulled into the gel or aggregate (and eventually the nanopore for sequencing).

The molecular recognition devices described herein can be used for at least one of sensing, identifying, and sequencing at least a portion of a target molecule as the target molecule translocates through a constriction. In one aspect, a method includes (i) providing an apparatus including a molecular recognition device described herein, the device being located in the apparatus such that a first chamber is located on the first side of the device and a second chamber is located on the second side of the device; (ii) introducing the target molecule into the second chamber; (iii) electrophoresing the target molecule so that it translocates through the constriction; and (iv) detecting an electrical signal when at least a portion of the target molecule is passing through the constriction.

The target molecule can be a polynucleotide. For example, the target molecule can be a DNA, RNA, or a portion thereof. The target molecule can be a polynucleotide including tens, hundreds, thousands, millions, or billions of nucleotides. The target molecule can also be an oligonucleotide.

In some embodiments, the method further includes threading a leading end of the target molecule through the constriction and into the first chamber, detecting said electrical signal. The electrical signal being detected is an electrical current or voltage. The electrical signal can also be recorded as a function of time.

In some embodiments, the method further includes obtaining at least one parameter reflective of an identification of a particular portion of the target molecule from the recorded electrical current. The at least one parameter can be charge, duration of current signal, shape of current signal, and decay of current. The method can further include comparing the at least one parameter with a predetermined threshold to determine whether the particular portion has been recognized. To improve recognition accuracy, electrical currents from a same portion of a predetermined number of copies of the target molecule can be detected.

One can measure the output of the sensing electrodes using a DNA molecule of known sequence. This permits one to correlate features in the measurement by the molecular recognition signal from the sensing electrodes.

In some embodiments, a device can be used to sequence DNA by the following set of steps: Step 1. A plurality of such nanopores, each functionalized to recognize one of the four bases, should be provided. This can be done using either serial reads or parallel reads. Step 2. Place DNA in lower chamber associated with each such nanopore. Optionally modify the DNA so as to allow entry into the pore from one direction only. In some embodiments, this can be done by tethering the DNA to a bead. Step 3. Electrophorese the DNA through the pore. If extra pulling force is needed, functionalize the end that passes through pore (after having been modified with e.g., biotin) and attach magnetic bead. Step 4. Pull DNA through by electrophoresis and/or magnetic bead. Step 5. Record current pulses as a function of time. Step 6. Align data from a plurality of reads for each type of base reader. Step 7. Align data from all 4 reads.

Any and all references to publications or other documents, including but not limited to, patents, patent applications, articles, webpages, books, etc., presented anywhere in the present application, are herein incorporated by reference in their entirety.

As noted elsewhere, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure can include methods, compositions, systems and apparatuses/devices which can further include any and all elements from any other disclosed methods, compositions, systems, and devices, including any and all elements corresponding to detecting one or more target molecules (e.g., DNA, proteins, and/or components thereof). In other words, elements from one or another disclosed embodiment can be interchangeable with elements from other disclosed embodiments. Moreover, some further embodiments can be realized by combining one and/or another feature disclosed herein with methods, compositions, systems and devices, and one or more features thereof, disclosed in materials incorporated by reference.

In addition, one or more features/elements of disclosed embodiments can be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments can contain negative limitations to note the lack of one or more features prior art teachings).

When describing the molecular detecting methods, systems and devices, terms such as linked, bound, connect, attach, interact, and so forth should be understood as referring to linkages that result in the joining of the elements being referred to, whether such joining is permanent or potentially reversible. These terms should not be read as requiring a specific bond type except as expressly stated.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements can optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in some embodiments, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements can optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in some embodiments, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, the term "about" when used in conjunction with numerical values and/or ranges generally refers to those numerical values and/or ranges near to a recited numerical value and/or range. In some instances, the term "about" can mean within ±10% of the recited value. For example, in some instances, "about 100 [units]" can mean within ±10% of 100 (e.g., from 90 to 110).

As used herein, the term "oligonucleotide" is defined as a molecule including two or more deoxyribonucleotides and/or ribonucleotides. Its exact size will depend on many factors, which in turn depend on the ultimate function or use of the oligonucleotide. The oligonucleotide can be derived synthetically or by cloning.

As used herein, the term "polynucleotide" refers to a polymer molecule composed of nucleotide monomers covalently bonded in a chain. DNA (deoxyribonucleic acid) and RNA (ribonucleic acid) are examples of polynucleotides.

References (Herein Incorporated by Reference):

Bai, J., D. Wang, S.-w. Nam, H. Peng, R. Bruce, L. Gignac, M. Brink, E. Kratschmer, S. Rossnagel, P. Waggoner, K. Reuter, C. Wang, Y. Astier, V. Balagurusamy, B. Luan, Y. Kwark, E. Joseph, M. Guillorn, S. Polonsky, A. Royyuru, S. P. Rao and G. Stolovitzky (2014). "Fabrication of sub-20 nm nanopore arrays in membranes with embedded metal electrodes at wafer scales." *Nanoscale:* 8900-8906.

Bhatia, R. B. and C. J. Brinker (2000). "Aqueous Sol-Gel Process for Protein Encapsulation." *Chem. Mater.* 12: 2434-2441.

Briggs, K., M. Charron, H. Kwok, T. Le, S. Chahal, J. Bustamante, M. Waugh and V. Tabard-Cossa (2015). "Kinetics of nanopore fabrication during controlled breakdown of dielectric membranes in solution." *Nanotechnology* 26(8): 084004.

Cherf, G. M., K. R. Lieberman, H. Rashid, C. E. Lam, K. Karplus and M. Akeson (2012). "Automated forward and reverse ratcheting of DNA in nanopore at 5-Å precision." *Nature Biotechnol.* 14: 344-348.

Ellerby, L. M., C. R. Nishida, F. Nishida, S. A. Yamanaka, B. Dunn, J. S. Valentine and J. I. Zink (1992). "Encapsulation of proteins in transparent porous silicate glasses prepared by the sol-gel method." *Science* 255(5048): 1113-1115.

Fologea, D., M. Gershow, B. Ledden, D. S. McNabb, J. A. Golovchenko and J. Li (2005). "Detecting single stranded DNA with a solid state nanopore." *Nano Lett.* 5: 1905.

Nisticò, R., P. Avetta, P. Calza, D. Fabbri, G. Magnacca and D. Scalarone (2015). "Selective porous gates made from colloidal silica nanoparticles." *Beilstein J. Nanotechnol.* 6: 2105-2112.

Nivala, J., D. B. Marks and M. Akeson (2013). "Unfoldase-mediated protein translocation though an alpha-hemolysin pore." *Nature Biotechnol.* 31: 247-250.

Tang, Z., Z. Liang, B. Lu, J. Li, R. Hu, Q. Zhao and D. Yu (2015). "Gel mesh as "brake" to slow down DNA translocation through solid-state nanopores." *Nanoscale* 7(31): 13207-13214.

Wanunu, M., W. Morrison, Y. Rabin, A. Y. Grosberg and A. Meller (2010). "Electrostatic focusing of unlabelled DNA into nanoscale pores using a salt gradient." *Nature Nanotechnology* 5: 160-165.

Yang, J., D. C. Ferranti, L. A. Stern, C. A. Sanford, J. Huang, Z. Ren, L.-C. Qin and A. R. Hall (2011). "Rapid and precise scanning helium ion microscope milling of solid-state nanopores for biomolecule detection, ." *Nanotechnology* 22: 285310-285320.

What is currently claimed is:

1. A molecular recognition device configured to perform at least one of sense, identify or sequence at least one portion of a target molecule, the device comprising:
   a partition having a first side and a second side, the partition characterized by a thickness associated therewith;
   a plurality of constrictions each having a first end open to the first side and a second end open to the second side, wherein:
     each of the plurality of constrictions includes an interior wall, each of the plurality of constrictions characterized by a diameter, a perimeter, and a length corresponding to the thickness;
     and
     the diameter is selected to pass therethrough target molecules from the first side to the second side, a single target molecule at a time;
   at least one pair of first and second sensing electrodes arranged within the plurality of constrictions between the first side and the second side of the partition, wherein
     the first electrode is arranged along at least a portion of the perimeter of the interior wall at a first position along the length of the plurality of constrictions,
     the second electrode is arranged along at least a portion of the perimeter of the interior wall at a second position along the length of the plurality of constrictions spaced away from the first position establishing a gap therebetween,
     and a partition material in the gap comprises an insulating material; and a layer of a porous material comprising a silicate gel on the first side of the partition by hydrolysis or spin-coating, wherein:
the porous material includes a porosity comprising a plurality of pores, the porous material is configured such that a target molecule passes through at least a portion of the porous material to reach the the plurality of constrictions, the average diameter of the pores of the porous material is about 10 nm or less and less than the diameter of each of the plurality of constrictions; and wherein the molecular recognition device is configured to establish an electric field for capture of the target molecule, the electric field extending a distance R from a center of each of the plurality of constrictions, wherein a portion of a height h of the layer of the porous material is less than R to establish a capture region for the target molecule that constrains the target molecule to approach a constriction comprising the plurality of constrictions along an edge of the constriction and to be pulled through the constriction along the interior wall to contact the first electrode and the second electrode.

2. The device of claim 1, wherein the amount of the porous material is such that the height of the layer of the porous material above the first side of the partition is less than about 5 microns.

3. The device of claim 2, wherein the amount of the porous material is such that the height of layer of the porous material above the first side of the partition is between about 10 nm to about 5 microns.

4. The device of claim 1, wherein the average diameter of the pores in the porous material is smaller than the diameter of a motor protein used to control the motion of a polymer.

5. The device of claim 1, wherein the first or second electrode comprises a metal or doped semiconductor.

6. The device of claim 1, wherein the plurality of constrictions is at least 100 constrictions.

7. The device of claim 6, wherein the plurality of constrictions is an array.

8. The device of claim 1, wherein the partition comprises a membrane.

9. A method for at least one of sensing, identifying, and sequencing at least a portion of a target molecule as the target molecule translocates through a constriction, the method comprising:

providing an apparatus comprising a molecular recognition device in accordance with claim 1, the device being located in the apparatus such that a first chamber is located on the first side of the device and a second chamber is located on the second side of the device;

introducing the target molecule into the first chamber;

electrophoresing the target molecule so that it translocates through the constriction; and detecting an electrical signal when at least a portion of the target molecule is passing through the constriction.

10. The method of claim 9, further comprising threading a leading end of the target molecule through the constriction and into the first chamber, detecting said electrical signal.

11. The method of claim 9, wherein the target molecule is a DNA or RNA molecule, or a portion thereof.

12. The method of claim 9, wherein the electrical signal being detected is an electrical current or voltage.

13. The method of claim 12, comprising:
recording the electrical current as a function of time; and
obtaining at least one parameter reflective of an identification of a particular portion of the target molecule from the recorded electrical current.

14. The method of claim 13, wherein the at least one parameter is selected from the group consisting of charge, duration of current signal, shape of current signal, and decay of current.

15. The method of claim 13, comprising comparing the at least one parameter with a predetermined threshold to determine whether the particular portion has been recognized.

16. The method of claim 12, comprising:
detecting electrical current from a same portion of a predetermined number of copies of the target molecule to thereby improve recognition accuracy of the portion.

17. The method of claim 9, configured for high-throughput sensing, identifying, or sequencing the target molecule.

* * * * *